(12) United States Patent
Ostrander et al.

(10) Patent No.: US 6,368,560 B1
(45) Date of Patent: Apr. 9, 2002

(54) PHOTOMETRIC GAS DETECTION SYSTEM AND METHOD

(75) Inventors: Clinton R. Ostrander, Atherton; Dale G. O'Harra, II, Belmont; Chuck McDowell, San Lorenzo; Steven J. Hartman, Menlo Park, all of CA (US)

(73) Assignee: Trace Analytical, Inc., Menlo Park, CA (US)

( * ) Notice: Subject to any disclaimer, the term of this patent is extended or adjusted under 35 U.S.C. 154(b) by 0 days.

(21) Appl. No.: 09/263,051

(22) Filed: Mar. 6, 1999

(51) Int. Cl.[7] .............................................. G01N 17/00
(52) U.S. Cl. ........................... 422/91; 422/80; 422/81; 422/82.09; 422/68.1; 422/82.05; 356/437; 356/440; 356/432
(58) Field of Search .............................. 422/91, 80, 81, 422/82.09, 82.05, 68.1; 356/410, 411, 440, 246, 318, 244, 437, 432; 436/73

(56) References Cited

U.S. PATENT DOCUMENTS

| 4,411,867 A | | 10/1983 | Ostrander |
| 5,120,129 A | * | 6/1992 | Farquharson et al. ....... 356/246 |
| 5,487,871 A | * | 1/1996 | McDow et al. ............... 422/80 |
| 5,792,663 A | * | 8/1998 | Fry et al. ....................... 436/73 |
| 5,815,276 A | * | 9/1998 | Fry ............................. 356/437 |
| 6,084,668 A | * | 7/2000 | McAndrew et al. ........ 356/246 |
| 6,188,475 B1 | * | 2/2001 | Inman et al. ............... 356/246 |

* cited by examiner

*Primary Examiner*—Jill Warden
*Assistant Examiner*—Brian Sines
(74) *Attorney, Agent, or Firm*—Oppenheimer Wolff & Donnelly, LLP

(57) ABSTRACT

A photometer including an elongated sample cell having a first end, a second end, and a passageway extending between the first end and the second end. Preferably, a ratio of a length of the sample cell to a lateral dimension of the passageway is at least 100 to 1. A first quartz window assembly is located at the first end of the sample cell and has a first port communicating with the passageway proximate to the first end, and a second quartz window assembly is located at the second end of the sample cell and has a second port communicating with the passageway proximate to the second end. An ultraviolet lamp is positioned to emit ultraviolet light through the first quartz window, the passageway, and the second quartz window, and an ultraviolet detector is positioned to receive the ultraviolet light emanating from the second quartz window. Preferably, the sample cell is operated at about ambient temperature, and the volume of the sample cell is no greater than about 0.2 cc to provide fast transient response and high sensitivity.

24 Claims, 7 Drawing Sheets

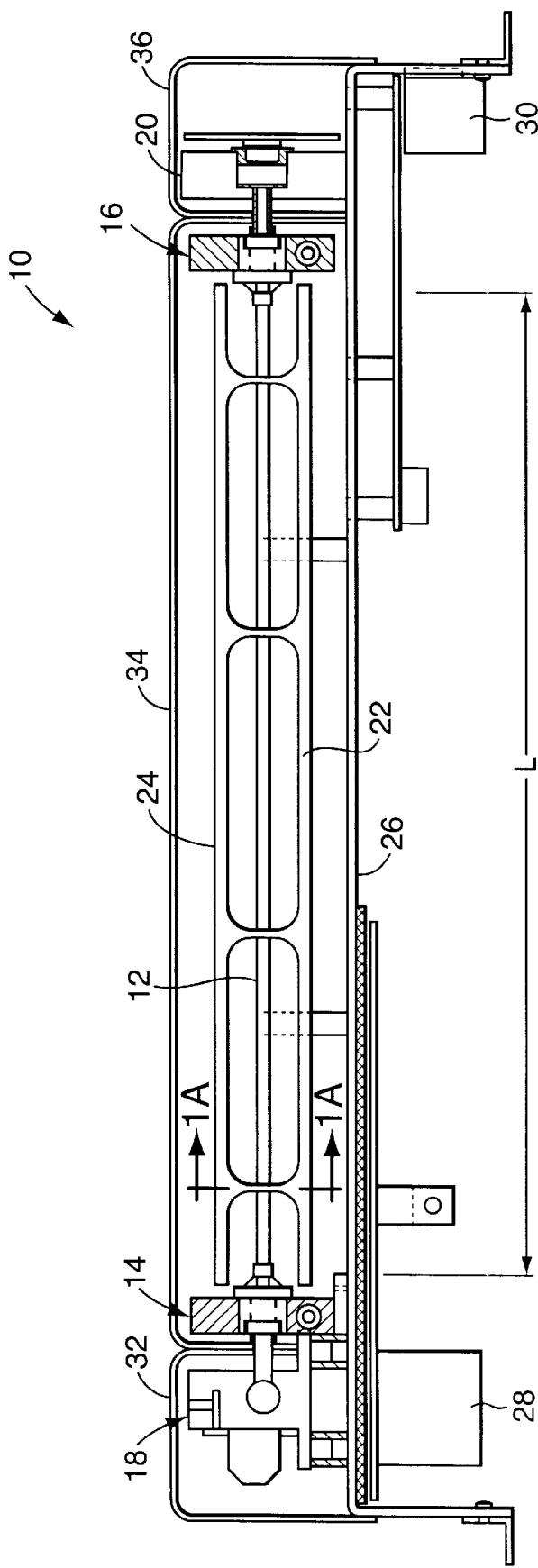
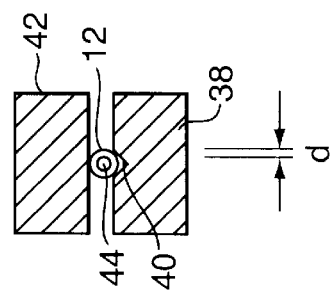
FIG. 1
FIG. 1A

PHOTOMETRIC GAS DETECTION SYSTEM AND METHOD

BACKGROUND OF THE INVENTION

This invention relates generally to the quantitative detection of concentrations of gases, and more particularly to methods and apparatus for detecting concentrations of a gas based on its reaction with mercuric oxide.

Reduction gas detectors operate on the principle of flowing a gas stream to be analyzed through a heated bed of mercuric oxide (HgO). Gases in the stream that can be oxidized (referred to as "reducing gases"), react with the mercuric oxide to produce free mercury vapor as shown in the following general reaction:

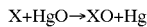

$$X + HgO \rightarrow XO + Hg$$

In this equation, X represents a reducing gas species and Hg is present as free mercury vapor. The mercury vapor produced in this reaction can be detected by its absorption of ultraviolet (UV) light within a sample cell forming a part of an ultraviolet photometer. An example of a reduction gas detector can be found in U.S. Pat. No. 4,411,867 of Ostrander, incorporated herein by reference.

Reactions with mercuric oxide are not specific to any particular gas species and a large number of reducing gases can react with mercuric oxide to produce mercury vapor. Gas measurement apparatus intended for quantitative measurements of specific gas species must therefore incorporate some process for isolating the gas species to be measured. One such apparatus is a gas chromatograph, which time-separates the gas sample into individual species. More particularly, this separation is obtained using a long tube or "column" through which flows a gas stream. The exit gas flow from the column is connected to the reduction gas detector and an apparatus for injecting a precise volume of sample gas into the gas stream is located upstream of the column. The column itself is packed with a granular substance which has the characteristic of separating the different gases comprising the sample based on their molecular size or other chemical properties. In the case of columns containing molecular sieve materials, small molecules such as $H_2$ will flow through the column faster than large molecules such as CO. It will therefore be appreciated that the difference in such properties cause each species or element of the sample to move through the column and into the detector at different times, and the gas species are detected as a series of Gaussian-shaped concentration "peaks." Starting from a single sample injection onto the column, each peak arrives at the detector in a characteristic time and the peak itself is essentially comprised of a single gas species. The height of each peak, or the integrated area under each peak, is representative of the concentration of the gas species.

In the prior art, reduction gas detectors have typically been operated at temperatures of 150–300° C. in order to promote the desired reactions with mercuric oxide. The sample cell as well as the mercuric oxide bed were heated in this temperature range in order to prevent mercury from condensing on the interior surfaces of the sample cell. As is well known to those skilled in the art, mercury vapor is quite condensable and adheres to relatively cool surfaces. Mercury condensation within the sample cell can result in slow equilibration of the sample cell to changing mercury concentrations and therefore slow time response of reduction gas detectors. Additionally, ultraviolet sample cells include quartz (i.e. pure $SiO_2$) windows which allow ultraviolet radiation to be transmitted through the cell. Mercury condensation on the quartz windows reduces the optical transmission of the cell due to absorption of the ultraviolet radiation by mercury condensation on the windows. This results in reducing signals for UV light sensors in the photometer, and correspondingly higher noise levels.

In general, gas detectors used in conjunction with gas chromatography must have relatively fast response times in order to accurately follow the concentration peaks created by the chromatography column. Additionally, typical gas chromatography flow rates are in the range of 20–60 cc/minute which are much lower than the 500–2000 cc/min flow rates associated with other gas measurement techniques (e.g. continuous analyzers). Gas chromatography detectors therefore preferably have small internal volumes in order to minimize concentration equilibration times to rapidly changing gas concentrations, and to reduce condensation of the flowing gas species as described previously.

Sample cells of the prior art, when embodied as a continuous sampling analyzer, were, of necessity, quite large in order to accommodate the large gas flows through the detectors. The large diameters of the prior art continuous sampling analyzer cells also transmitted relatively large quantities of ultraviolet radiation, which was desirable to reduce noise levels in the detector output signal. Sample cells of the prior art for chromatography detectors were smaller than those used for continuous sampling detectors but were still limited to a minimum diameter of 0.15 cm and a maximum length of 10 cm which were the dimensions that could still transmit adequate amounts of ultraviolet light through the passageway of the cell. That is, the diameter of the passageway of the cell was kept fairly large and the length of the cell was kept fairly short, so that a sufficient amount of light from the ultraviolet source could travel through the cell and still be detected by the ultraviolet (UV) sensor. This is because ultraviolet sources are non-coherent and, therefore, the amount of light impinging upon the UV detector is directly proportional to the diameter of the cell passageway and is inversely proportional to the square of the length of the cell. Hence, short, large diameter cells were the norm in the prior art.

The temperature of prior art chromatography detector cells were maintained at the same temperature as the HgO beds which, in practice, was in the range of 265–285° C. Based on this relatively high temperature, the optical windows of the cell were constructed of relatively long quartz rods (approximately 5 cm in length) in order to isolate the hot cell from the temperature-sensitive ultraviolet lamp and light sensor. The amount of UV light transmitted through these rods is also quite dependent on temperature of the rod and, therefore, minor changes in rod temperature affect the amount of light impinging on the UV sensor. Minor variations in convective cooling of the rods of the prior art heated detector cells therefore introduced variations in light transmitted through the cell which were not due to mercury vapor concentration. The net affect of these variations was to increase drift and noise in the output of the light sensor.

It will therefore be appreciated that the performance of the prior art chromatography cell was limited by: a) the relatively large cell diameter and short length required for transmission of suitable levels of UV light; b) the relatively large condensation surface area of the cell due to its diameter and length; and c) the relatively high cell temperature which necessitated the requirement for optical windows comprised of quartz rods which added thermally-induced drift and noise to the detector output.

Since the sensitivity of mercury detection is directly proportionate to cell length, the ideal sample cell would be infinitely long and have zero diameter, zero internal volume, and zero internal surface area when one ignores other factors such as the amount of light in gas that could travel down the passage way of such an ideal sample cell. Additionally, the optical cell windows, if heated, would ideally be infinitely thin and therefore not prone to produce thermal convection errors.

SUMMARY OF THE INVENTION

A preferred embodiment of the present invention is directed to an improved photometer for detecting mercury vapor in a low flow-rate carrier gas. As such, it is well suited for gas chromatography for species that can be reduced in a heated mercuric oxide bed.

The sample cell of the improved photometer of the present invention is long and thin, as compared to sample cells of the prior art. The low internal surface area has eliminated the need to heat the cell, which permits very thin optical cell windows, which are essentially not prone to the production of thermal convention errors. The present invention stabilizes the temperature of an intense UV light source to provide sufficient, low noise UV light through the long, thin sample cell. As such, a fast, highly sensitive, and reliable photometer is provided by the method and apparatus of the present invention.

A preferred embodiment of the present invention therefore relates to detecting small concentrations of gases by measuring the spectral absorption of mercury vapor produced by those gases in a reduction process with a heated mercuric oxide bed. The apparatus includes an elongated cylindrical sample cell preferably operated at ambient temperatures and optimized to have a long passageway to increase the sensitivity of the photometer. A quartz window assembly is provided at each end of the sample cell such that ultraviolet light can be directed into a first window assembly, through the passageway of the sample cell, and out of a second window assembly to impinge upon an ultraviolet detector.

By providing a sample cell that is very long in proportion to the diameter of the passageway the need for heating the sample cell has been eliminated. Preferably, the sample cell is made from stainless steel, aluminum, or borosilicate glass. Also preferably, the ratio of the length of the sample cell to the diameter of the passageway through the sample cell is at least 100 to 1, which reduces internal surface area upon which mercury can condense and which increases the sensitivity of the cell.

The quartz window assemblies are preferably provided with individual heaters to encourage the evaporation of condensates on the windows. The ultraviolet lamp is also preferably provided with a heater, a heat sink, and closed loop control system to maintain the temperature of the lamp within precise limits. The elongated sample cell is preferably held in a V-block arrangement to provide a straight optical path through the passageway of the sample cell.

It will therefore be appreciated that a photometer of the present invention includes an elongated sample cell having a first end, a second end, and an elongated passageway extending between the first end and the second end. Preferably, a ratio of a length of the sample cell to a lateral dimension of the passageway is at least 100 to 1. Furthermore, the cell is preferably maintained at about ambient temperature. A first quartz window assembly is located at the first end of the sample cell and has a first port communicating with the passageway proximate to the first end, and a second quartz window assembly is located at the second end of the sample cell and has a second port communicating with the passageway proximate to the second end. A source of electromagnetic radiation (preferably UV radiation) is positioned to emit electromagnetic radiation through the first quartz window, the passageway, and the second quartz window, and a detector of electromagnetic radiation (preferably a UV detector) positioned to receive electromagnetic radiation emitted through the second quartz widow. Preferably, the sample cell is operated at about ambient temperature, and the volume of the sample cell is no greater than about 0.2 cc to provide fast transient response.

A method for measuring mercury vapor concentration in accordance with the present invention includes flowing a carrier gas through a mercuric oxide bed and then through a passageway of an elongated sample cell, where the sample cell has a length and the passageway has a lateral dimension such that a ratio of the length to the lateral dimension is at least 100 to 1. An ultraviolet light is directed through the cell to impinge upon a detector, and an output signal of detector is zeroed. Next, a gas sample is inserted into the flow of the carrier gas, where the gas sample comprises one or more substances that can be reacted with a mercuric oxide bed to form a mercury vapor. Finally, the output signal of the detector is analyzed.

The present invention provides a number of advantageous features over the prior art. For one, the sample cell is not heated, eliminating costly and potentially unreliable heaters and heater control systems. Furthermore, by not heating the cell, the quartz windows can be made much shorter than in the prior art, eliminating the noise component caused by small localized variations in temperature due to convention currents. Finally, the long sample cell of small diameter provides superior sensitivity and faster response time than shorter, wider cells of the prior art.

These and other advantages of the present invention will become apparent upon a reading of the following detailed descriptions and a study of the several figures of the drawings.

BRIEF DESCRIPTION OF THE DRAWINGS

FIG. 1 is a side elevational view of the gas detector of the present invention;

FIG. 1A is a cross-sectional view taken along line 1A–1A of FIG. 1;

DETAILED DESCRIPTION OF THE PREFERRED EMBODIMENTS

Figure 2:
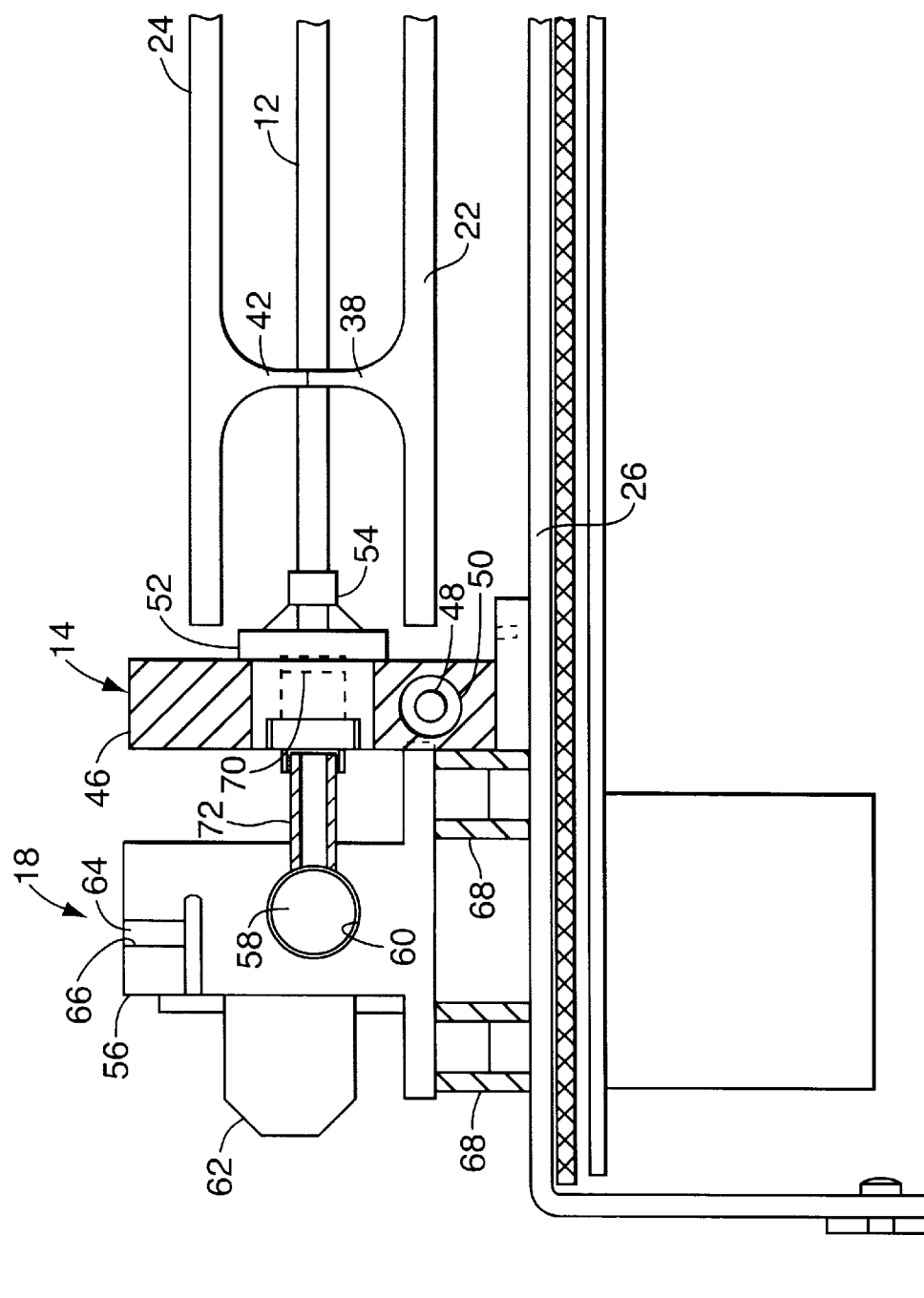
FIG. 2 is an enlarged, cross sectional view of the of the lamp end assembly of the present invention.

In FIG. 1, a photometer 10 in accordance with the present invention includes an elongated sample cell 12, a first quartz window assembly 14, a second quartz window 16, a lamp assembly 18, and a detector assembly 20. The sample cell 12 is supported by a V-block unit 22 and is held in place by a clamp unit 24. The various components are supported by a base 26, which can further support other components such as a lamp inverter 28 and detector output electronics 30. During operation, many of the components are covered with one or more covers 32, 34, and 36.

As seen in FIG. 1, the sample cell is an elongated structure, preferably formed as a tube, having a length L which, in a preferred embodiment of the present invention, is about 30 cm. With additional reference to the cross-sectional view of FIG. 1A, the sample cell is supported by a plurality of V-groove blocks 38 having V-grooves 40 and is held in place by clamp 42. The long sample cell 12 requires precise alignment to allow the UV light to shine down the internal passageway without excessive loss. The V-groove blocks 38 provide this support and alignment. Similar V-groove block arrangements have been used in the laser arts to precisely align laser rods, as will be appreciated by those skilled in the art. The clamps 42 hold the sample cell 12 firmly within the V-grooves 40 of the V-groove blocks 38.

As can also be seen in FIG. 1A, the cell 12 is provided with a passageway 44. Preferably, this passageway is a cylindrical bore or the like, such that the lateral dimension "d" of the passageway is, essentially, the diameter of the bore. Alternatively, the passageway may not be cylindrical, in which case a maximum lateral dimension is defined as the maximum diameter of the bore taken perpendicularly to an axis of the cell. However, the walls of the passageway should be smooth (e.g. electropolished or hydraulically bored) to a finish of 20 RA or less to inhibit mercury from adhering to the surface.

It should be noted that the sample cell 12 is very long in relation to the lateral dimension of the passageway 44. In the present example, the passageway is cylindrical (the cell 12 forming a tube) such that the lateral dimension d is about 0.040 cm in diameter. Since the length L of the cell 12 is 30 cm in this example, the ratio of the length L to the lateral dimension d is L/d=750:1. This provides very good sensitivity, quick response time, and minimal internal surfaces (wall area) of the passageway 44 to which mercury can stick. However, if higher volumes of sample gas and/or greater lamp intensity is desired at the detector, this ratio can be reduced to as little as 100:1 in some instances, although it is preferable that it is at least 250:1. It is desirable, nonetheless, to have a total cell volume of no more than about 0.2 cc, in this preferred embodiment.

The material of the sample cell is preferably one or more of a borosilicate glass, stainless steel, or aluminum. If the sample cell is made from a borosilicate glass, it is preferably encased in a stainless steel tube for protection.

It has been found that by providing a ratio of cell length to passageway diameter of less at least 100:1 that the heater required in prior art reduction gas detectors can be eliminated. That is, the cell 12 can be operated below about 150° C., in contrast to sample cells of the prior art. In fact, the cell 12 can be operated below 100° C. and even at ambient temperatures (about 25° C.) without creating a substantial problem from the condensation of mercury vapor on the inner walls of the passageway.

In FIG. 2, the first quartz window assembly 14 and the lamp assembly 18 are shown in greater detail. The first quartz window assembly includes a heater block 46 provided with a resistive heater 48 in a bore 50. The heater block is preferably made from a suitable metal such as aluminum, and serves to stabilize the heat from the resistive heater 48. A window unit 52 is attached to the cell 12 by a fitting 54. If the sample cell 12 is stainless steel, the fitting 54 is preferably brazed to the sample cell. If the sample cell is borosilicate glass, the fitting is preferably glued to the sample cell with a suitable adhesive.

The lamp assembly 18 includes a heater block 56 made, again, preferably from a good thermal storage material such as aluminum. A lamp 58 is preferably positioned within a bore 60 in the heater block 56. In this preferred embodiment, the lamp is an ultraviolet (UV) lamp having operating frequency centered at about 254 nanometers, and is available from a variety of sources. For example, such lamps are commercially available from BHK, Inc. of Claremont, Calif. A resistive heater 62 is coupled to the heater block, and a thermocouple 64 is disposed within a bore 66 of the heater block 56. Heat sinks 68 couple the heater block 56 to the base 26 to draw heat from the heater block. The heat sinks 68 are preferably made from the same metal as the heater block 56.

It is desirable that the heater 62 and the heat sinks 68 have about the same time constants. This makes it easier to maintain the temperature of the lamp assembly 18 with a very tight tolerance (e.g. within about 0.05 degree centigrade) when forming a part of closed-loop temperature controller, as will be discussed in greater detail subsequently. It is important to maintain this accurate temperature control since the present invention does not utilize a reference detector proximate to the lamp 58, as was the case in the prior art. By maintaining a very accurate fixed temperature on the lamp 58, the UV light output by the lamp will be a constant, eliminating the need for such a reference detector. A tube 72 preferably metal) extends from the lamp 58 to the quartz window 70 to shade that portion of the optical path from stray ambient light.

It is to be re-emphasized that, in the past with other instruments, a reference detector was required to produce a signal Vref that was used in conjunction with the output signal Vsig of the main detector to create the output signal Vout. In practice, these two signals could not be accurately measured with any consistency. In the prior art, the output signal Vout was calculated by the log(Vref/Vsig). By stabilizing the temperature of the ultraviolet source, the reference signal Vref becomes a constant and does not have to be measured. Also, as long as the mercury vapor concentration is less that 50 parts per billion (ppb) in a 30 cm long cell, the changes in the detected signal Vsig are so small that it is approximately linearly proportional to logVsig. That is, when the mercury vapor concentration is less than about 2 ppb per centimeter of cell length, the output signal from the detector is generally linearly proportional to the absorption of ultraviolet radiation by mercury vapor in the cell. As a result, the output signal Vout becomes essentially equivalent to the detected signal Vsig. Thus, with the present invention not only is the need for a reference detector eliminated, but also costly logarithmic processing of the signal is eliminated.

Figure 3:
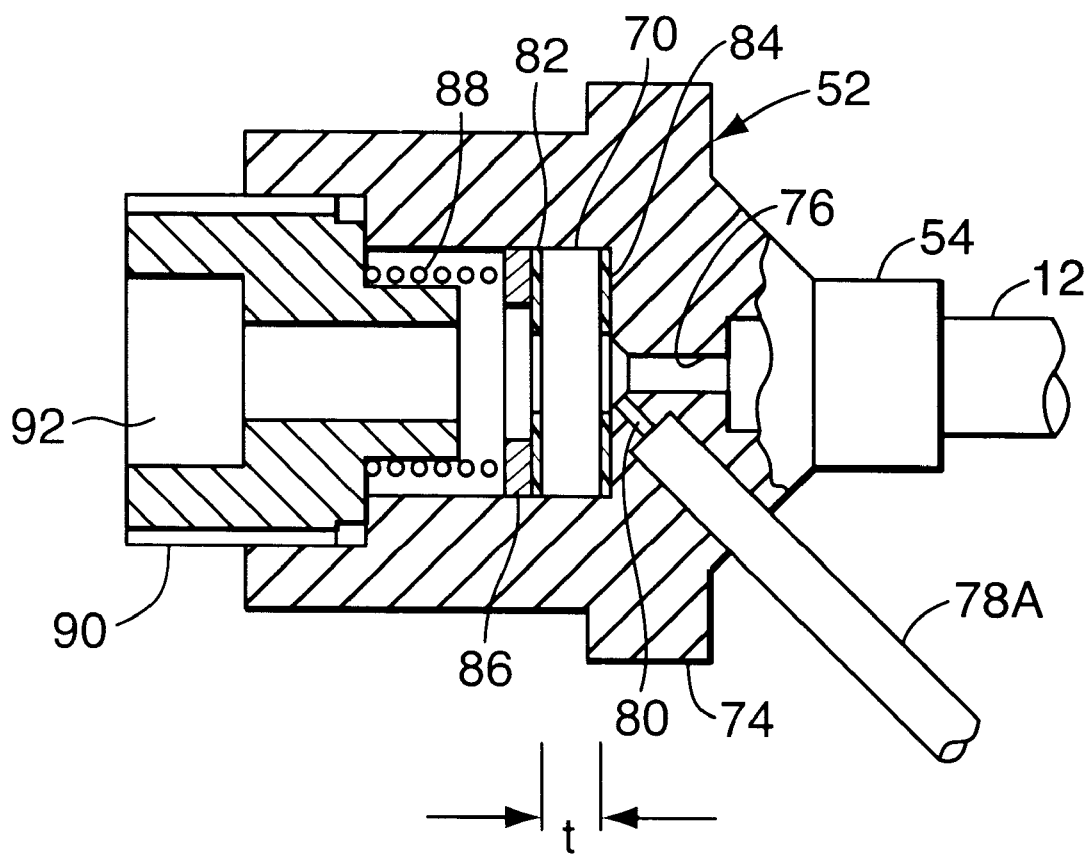
FIG. 3 is an enlarged cross sectional view of the quartz window assembly of the present invention.

In FIG. 3, a window unit 52 is shown in cross-section. The window unit includes a body that is coupled to the sample cell 12 by the fitting 54. A small bore 76 communicates with the passageway of the cell 12. A feed tube 78A forms a port 80 which communicates with the bore 76 and, therefore, the passageway of the sample cell. In this embodiment, the port 80 is an outlet port for injecting gas into the sample cell, although it could equally well be an inlet port releasing gas from the sample cell. A disk-shaped quartz window 70 is sandwiched between two Teflon washers 82 and 84. A more rigid washer 86 (e.g. a metal washer) forms a bearing surface for a spring 88 which is held in place by a retainer bolt 90. The window unit 52 therefore forms a gas-tight seal to the end of the sample tube 12 with only gas port 80 for the ingress or egress of gas. A bore 92 in the bolt 90 is receptive to the light guide 72.

It should be noted that the thickness "t" of the quartz window 70 is much less than that required in the prior art. This is because the sample cell is operated at lower temperatures than in the prior art, and a thick window is not required to dissipate the heat of the sample cell. As such, the quartz window is much less susceptible to changes in the index of refraction due to large temperature gradients along its length. In this preferred embodiment, the thickness t of the window is about 2.5 millimeters. Preferably, the thickness is no greater than 1.25 millimeters, and preferably it is less than 0.625 millimeters, and most preferably is no thicker than is required for structural integrity.

By heating the window 70 to a temperature of at least about 80° C. with the heater 48 and heater block 46, any mercury condensate on the window 70 can be cause to evaporate over time. This "cleaning" feature enhances the operation of the window 70 by permitting more light to enter the sample cell. While at least about 80° C. is one preferred temperature range in which to heat the windows, a temperature of about 50° C. or greater can also be used.

Figure 4:
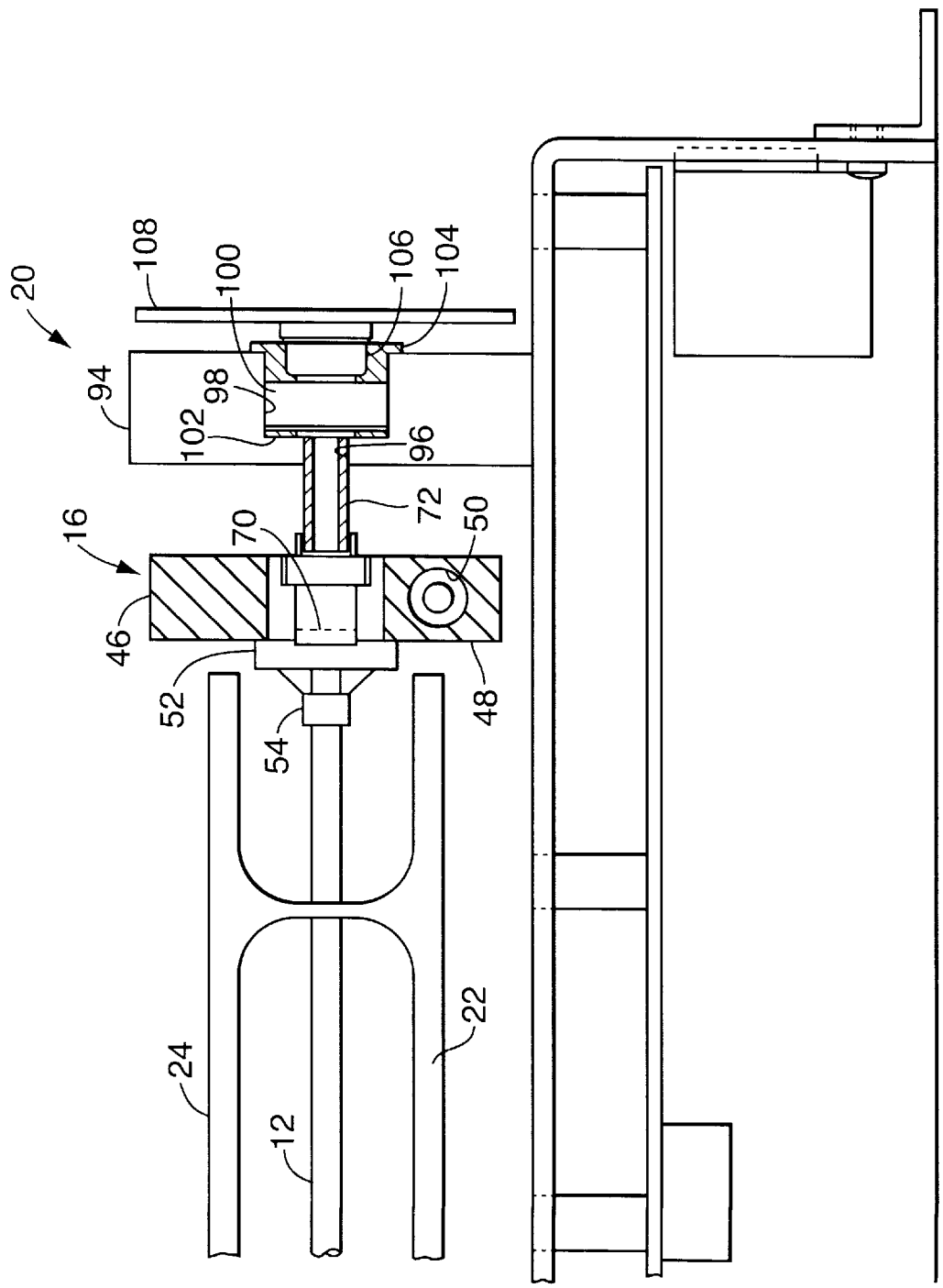
FIG. 4 is an enlarged cross sectional view of the detector end assembly of the present invention.

In FIG. 4, the window assembly 16 and detector assembly 20 are shown in cross section. The window assembly 16 is of essentially the same construction as the window assembly 14 described previously, but is oriented in the opposite direction. Therefore, the construction of window assembly 16 can be considered to be a mirror image of the construction of window assembly 14. The same numerals have been used to indicate the same elements in window assemblies 14 and 16.

The detector assembly 20 includes a mounting block 94 having a first bore 96 receptive to a tube 72 (which blocks stray ambient light from the light path) and a second bore 98 receptive to a UV filter 100. The filter 100 is retained by a washer 102 and a nut 104. An ultraviolet detector 106 can be mounted on a printed circuit (PC) board 108, as will be appreciated by those skilled in the art. UV detector 106 is commercially available from a number of sources such as EG&G Electro-Optics Division of Salem Mass. and Hamamatsu Photonics, K.K. of Hamamatsu City, Japan.

Figure 5:
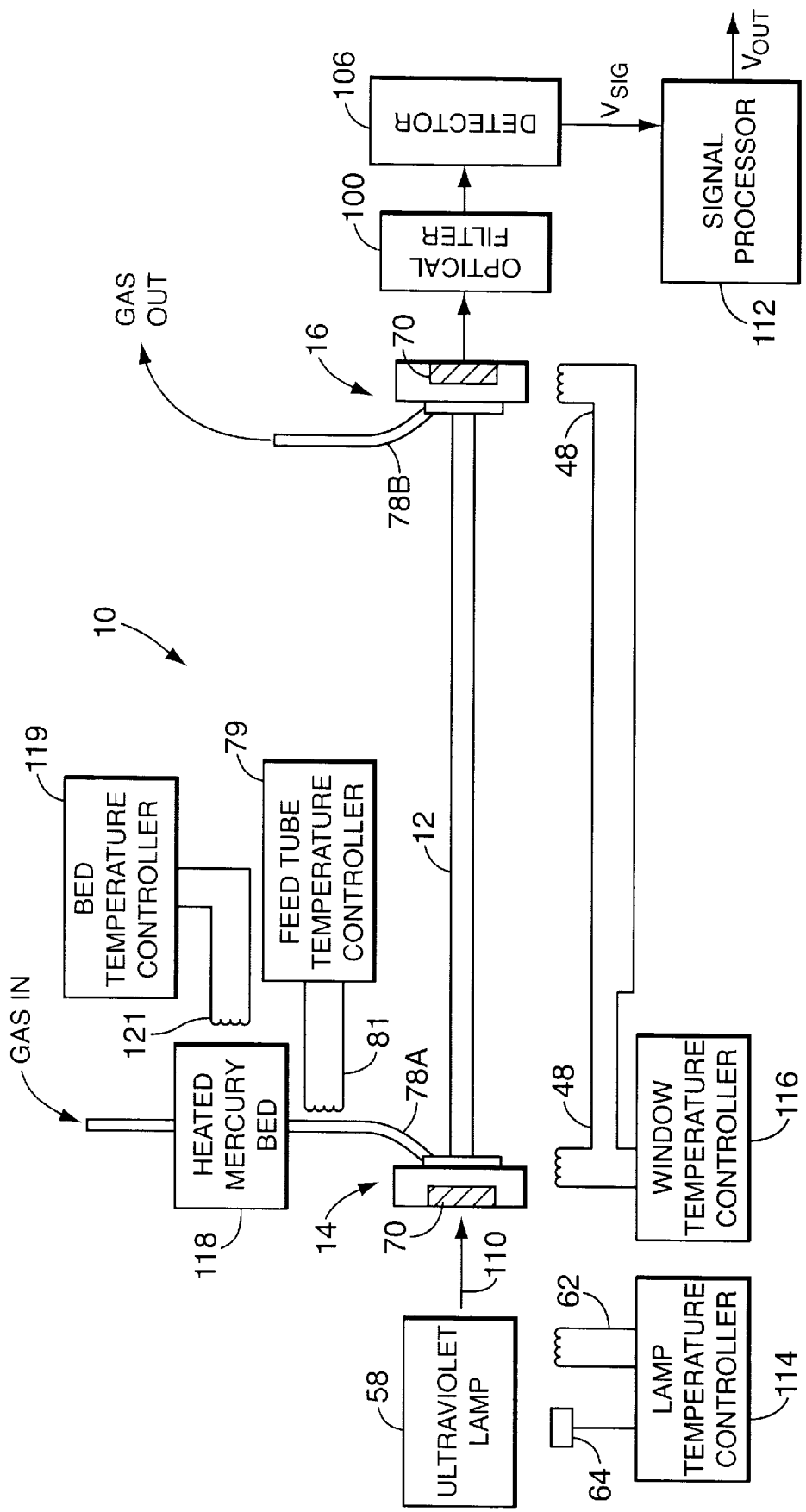
FIG. 5 is a block diagram that illustrates the functional elements and operation of the present invention.

In FIG. 5, a functional block diagram of the photometer 10 will be used to describe the operation of the present invention. Items previously described are shown in a diagrammatic form and are referenced with the same numerals as previously used. The UV lamp 58 produces UV light 110 which goes through quartz window 70 of window assembly 14, through the passageway of sample cell 12, through the quartz window 70 of the window assembly 16, through optical filter 100, and impinges upon detector 106. The detector 106 produces a signal Vsig, which is processed in a signal processor (e.g. an analog-to-digital (A/D) converter) to produce a digital signal Vout which represents the concentration of mercury vapor in the sample cell 12 and, therefore, the concentration of the reduced gas being measured in the sample.

A temperature controller 114 is used to maintain the temperature of the UV lamp 58. More particularly, the controller 114 is responsive to an output of the thermocouple 64 and controls the current flowing through heater 62. The heat sink arrangement described previously aids in the precise maintenance of the lamp temperature using this closed-loop feedback system.

A window temperature controller 116 likewise controls the temperature of the quartz window 70 by controlling the current flowing through the heaters 48. The temperature of the windows are, in this example, maintained at about 80° C. to provide self-cleaning of deposited materials. Preferably, the temperature is maintained at a constant level with a feedback loop type controller, as described previously.

There may be one or more temperature controllers associated with the heated mercury bed 118 and the feed tube 78A. A bed temperature controller 119 controls a resistive heater 121 to maintain the bed 118 within an operating temperature range (e.g. 265–285° C.), as is well known to those skilled it the art. An optional feed tube temperature controller 79 controls a resistive heater 81 to inhibit condensation of mercury vapor within feed tube 78A. Like the windows, the feed tube is preferably heated to at least about 50° C., and more preferably about 80° C. or more. These and the other temperature controllers preferably under the control of a master system controller (not shown).

In operation, a mercury oxide bed 118 is heated by heater 121, and a sample gas is caused to flow through the mercury oxide bed. Gaseous components that can be oxidized will be reduced by the mercury oxide bed, resulting in the creation of mercury vapor which flows through tube 78A, through the sample cell 12, and out an outlet tube 78B along with the carrier gas. Since mercury vapor strongly absorbs UV light, the detected light level will drop as the mercury vapor level within the cell 12 rises. The resulting waveform can be analyzed to determine the concentration levels of the reduced gases in the carrier gas.

Figure 6:
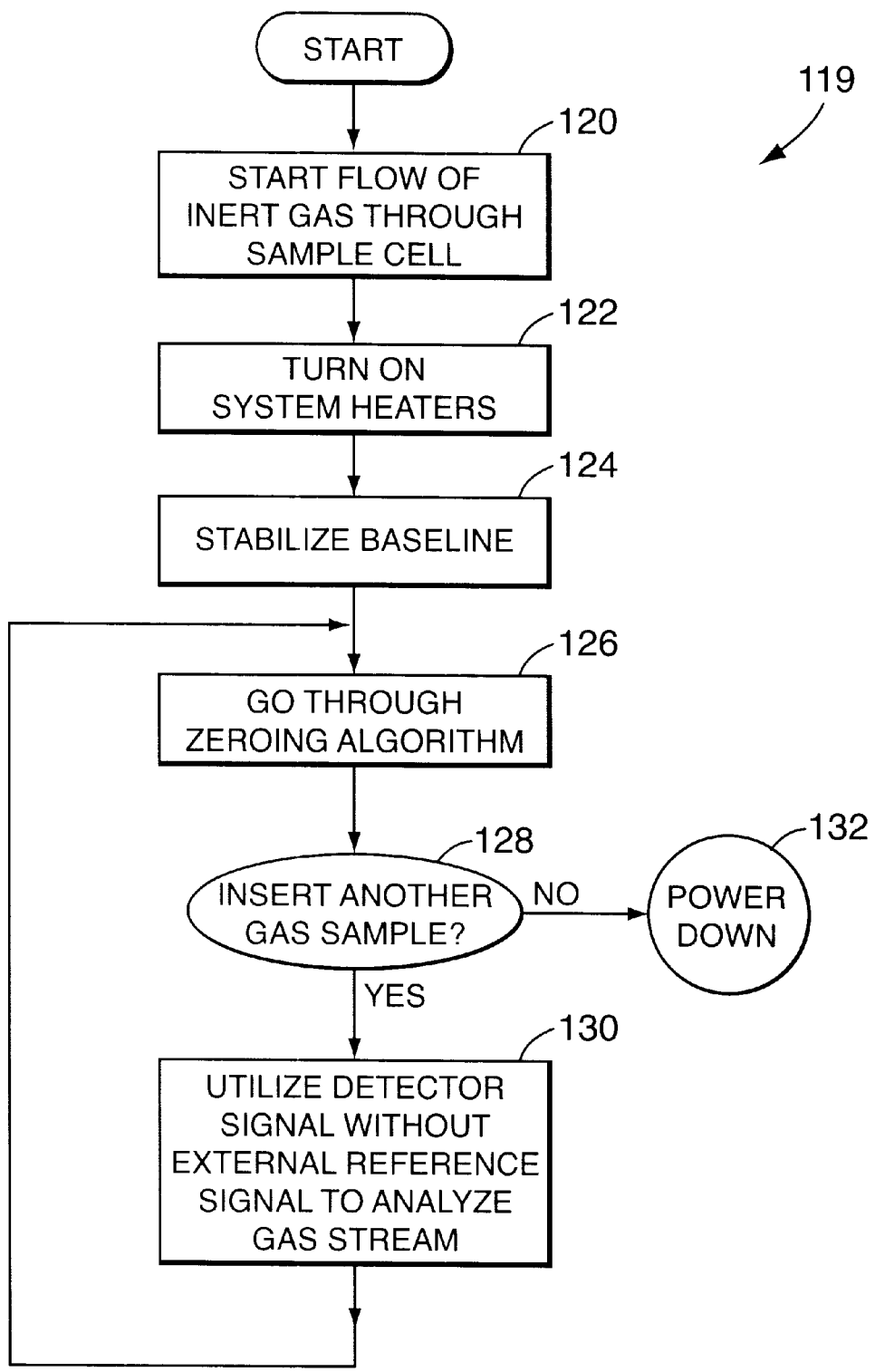
FIG. 6 is a flow diagram illustrating the operations involved in detecting small concentrations of gases in accordance with the present invention.

FIG. 6 is a flow diagram illustrating the operations (process) 119 performed by the gas detection instrument to detect and analyze small concentrations of gases in accordance with the present invention. First, an inert gas is caused to flow through the sample cell in an operation 120. Next, in an operation 122, the system heaters are turned on. For example, window heaters 48, lamp heater 64, and bed heater 121 are turned on at this time. If there is a feed tube heater 81, it is also turned on at this time. Controlled by the lamp temperature controller 114, the lamp heater 62 applies the proper amount of heat to the heater block in order to precisely stabilize the temperature of the ultraviolet lamp, which in turn stabilizes the operating frequency, reduces noise, and otherwise enhances the performance of the ultraviolet lamp.

With the inert gas flowing and the heaters on, the gas detector is then stabilized, e.g. for about 15 minutes or more, in an operation 124. This "Stabilize Baseline" operation 124 is sometimes referred to as "baseline stabilization", since it provides a baseline reference against which subsequent measurements can be compared.

After baseline stabilization, the detector goes through a zeroing algorithm in an operation 126. This operation 126 is discussed in greater detail below with reference to FIG. 7. Briefly, with the presence of a gas sample to be analyzed flowing through the sample cell, the gas detector in operation 126 uses a zeroing algorithm to establish a zero baseline output by the detector prior to the injection of the sample.

In operation 128 it is determined whether another gas sample is to be injected into the carrier gas stream. If there is, in an operation 130, the detector is utilized to analyze the concentration of mercury vapor in the carrier gas, as previously described. Process control then returns to operation 126 to prepare for a possible additional sample. If there are no more samples to be injected, the system is powered down as indicated at 132.

Figure 7:
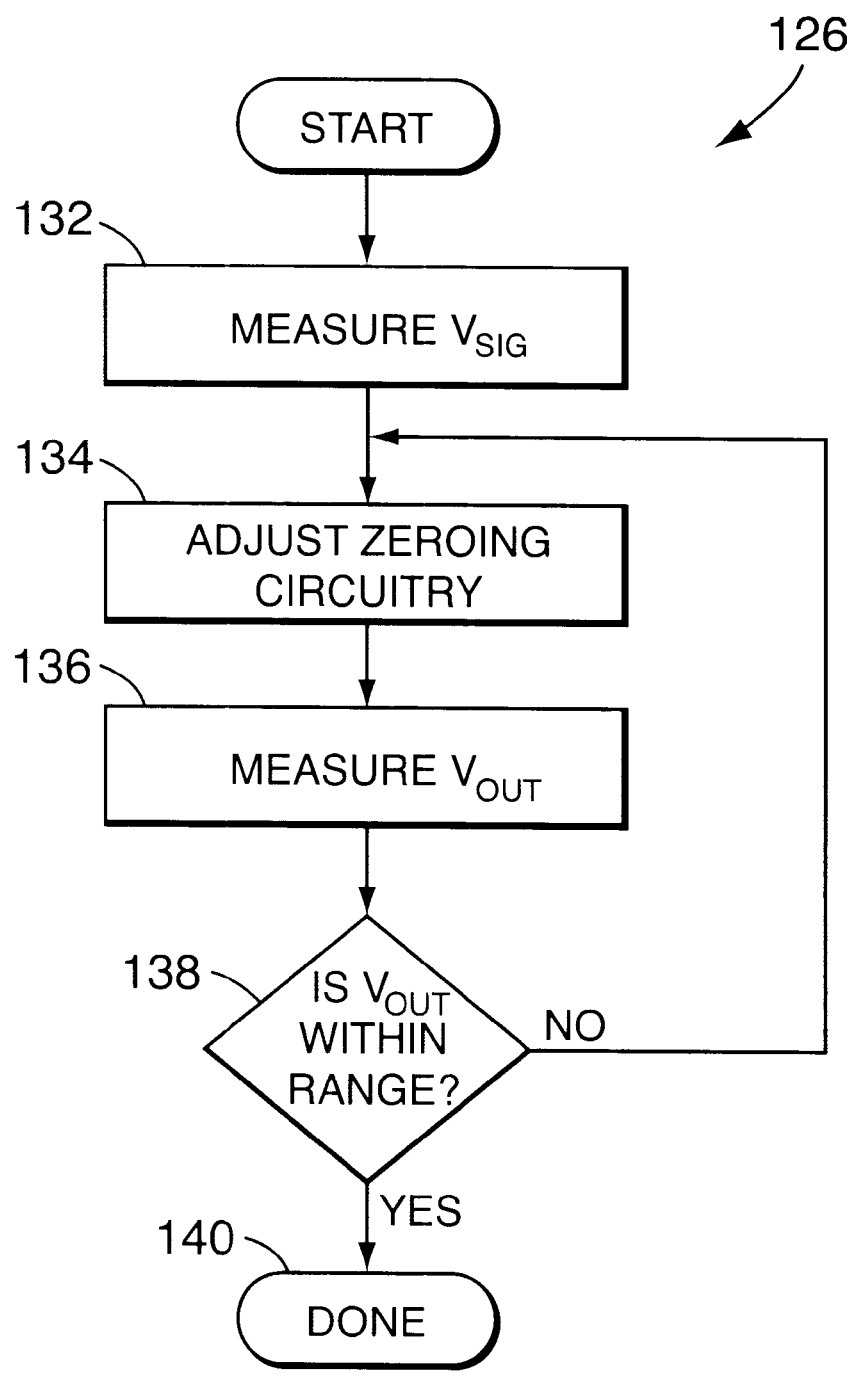
FIG. 7 is a flow diagram illustrating the operations involved in zeroing the photometer of the present invention.

In FIG. 7, the operation 126 of performing the zeroing algorithm is described in greater detail. To set the baseline signal, signal Vsig in operation 132 is measured. To insure that the signal is Vout is in a proper range, the zeroing circuitry (typically an operational amplifier controlled by a D/A converter) is adjusted in an operation 134, as will be appreciated by those skilled in the art. The output signal Vout is then measured in an operation 136. If the signal Vout is out of range, process control is returned to operation 134 to again adjust the zeroing circuitry (not shown). When the signal Vout is within range as determined by operation 138, the process is complete as indicated at 140.

Although the foregoing invention has been described in some details for purposes of clarity and understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A photometer comprising:
   an elongated sample cell operating at a temperature below about 150° C. having a first end, a second end, and an elongated passageway extending between said first end and said second end, said elongated passageway having a lateral dimension, where a ratio of a length of said sample cell to said lateral dimension is at least 100 to 1;
   a first quartz window assembly disposed at said first end of said sample cell and having a first port communicating with said passageway proximate to said first end;
   a second quartz window assembly disposed at said second end of said sample cell and having a second port communicating with said passageway proximate to said second end;
   a source of electromagnetic radiation positioned to emit electromagnetic radiation through said first quartz window, said passageway, and said second quartz window; and
   a detector of electromagnetic radiation positioned to receive electromagnetic radiation emitted through said second quartz widow by said source of electromagnetic radiation.

2. A photometer as recited in claim 1 wherein said sample cell has an operating temperature that does not exceed 100° C.

3. A photometer as recited in claim 2 wherein said sample cell is operated at about ambient temperature.

4. A photometer as recited in claim 1 wherein said volume of said sample cell is no greater than about 0.2 cc.

5. A photometer as recited in claim 1 wherein said first window assembly includes a first quartz window sealed against said first end of said passageway with said first port in fluid communication with said passageway and wherein said second window assembly includes a second quartz window sealed against said second end of said passageway with said second port in fluid communication with said passageway.

6. A photometer as recited in claim 1 wherein said source of electromagnetic radiation comprises an ultraviolet lamp.

7. A photometer as recited in claim 5 wherein said first quartz window and said second quartz window have a thickness of no greater than 2.5 millimeters.

8. A photometer as recited in claim 7 wherein said first quartz window and said second quartz window have a thickness of no greater than 1.25 millimeters.

9. A photometer as recited in claim 5 further comprising a first window heater associated with said first window assembly and a second window heater associated with said second window assembly.

10. A photometer as recited in claim 9 wherein said first window heater maintains said temperature of said first window assembly at a minimum temperature of about 50° C. to induce evaporation of condensate on said first quartz window, and wherein said second window heater maintains said temperature of said second window assembly at a minimum temperature of about 50° C. to induce evaporation of condensate on said second quartz window.

11. A photometer as recited in claim 10 wherein said first window assembly and said second window assembly are maintained at temperatures of at least about 80° C.

12. A photometer as recited in claim 10 further comprising a first heat sink coupled to said first window assembly, a second heat sink coupled to said second window assembly, and a window temperature controller coupled to said first window heater and said second window heater.

13. A photometer as recited in claim 12 wherein said first window heater and said first heat sink have similar time constants, and wherein said second window heater and said second heat sink have similar time constants.

14. A photometer as recited in claim 1 further comprising a plurality of V-block supports supporting said elongated sample cell.

15. A photometer as recited in claim 14 further comprising a plurality of clamps associated with said plurality of V-blocks, whereby said sample cell is clamped to said plurality of V-blocks with said plurality of clamps.

16. A photometer as recited in claim 6 wherein one of said first port and said second port is an inlet, and wherein said other of said first port and said second port is an outlet.

17. A photometer as recited in claim 16 further comprising a mercuric oxide bed associated with said inlet, whereby a fluid sample can be caused to flow through said mercuric oxide bed, said inlet, said passageway, and out of said outlet.

18. A photometer as recited in claim 17 further comprising a feeder tube coupling said mercuric oxide bed to said inlet, wherein said feeder tube is heated to at least about 50° C.

19. A photometer as recited in claim 18 wherein said feeder tube is heated to at least about 80° C.

20. A photometer as recited in claim 1 wherein a material of said sample cell comprises at least one of stainless steel, aluminum, and a borosilicate glass.

21. A photometer as recited in claim 20 wherein said material of said sample cell which forms said passageway consists essentially of stainless steel.

22. A photometer as recited in claim 20 wherein said material of said sample cell which forms said passageway consists essentially of borosilicate glass.

23. A photometer as recited in claim 22 wherein said borosilicate glass comprises a glass tube, and wherein said material of said sample cell further includes a stainless steel tube surrounding said glass tube.

24. A photometer as recited in claim 17 wherein an output signal from said detector is generally linearly proportional to said absorption of ultraviolet radiation by mercury vapor within said cell when said concentration of said mercury vapor is less than about 2 parts per billion per centimeter of cell length.

* * * * *